US00PP34761P2

(12) United States Plant Patent
van Langen

(10) Patent No.: US PP34,761 P2
(45) Date of Patent: Nov. 22, 2022

(54) ***ECHEVERIA* PLANT NAMED 'AMIECH2104'**

(50) Latin Name: *Echeveria agavoides*
Varietal Denomination: 'AMIECH2104'

(71) Applicant: NovoAmi B.V., Heerhugowaard (NL)

(72) Inventor: Gerard van Langen, Heerhugowaard (NL)

(73) Assignee: NovoAmi B. V., Heerhugowaard (NL)

( * ) Notice: Subject to any disclaimer, the term of this patent is extended or adjusted under 35 U.S.C. 154(b) by 0 days.

(21) Appl. No.: 17/803,334

(22) Filed: May 14, 2022

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Karen M Redden
(74) *Attorney, Agent, or Firm* — Samuel R. McCoy, Jr.

(57) ABSTRACT

A new and distinct *Echeveria agavoides* plant named 'AMIECH2104' which is characterized by thick, durable foliage loosely arranged in a basal rosette, foliage that is conspicuously curled upward distally, light yellow-green to green juvenile foliage with very light greyed-green margins at the center of the rosette, foliage which becomes progressively darker as it matures, transitioning to dark greyed-green with greyed-orange foliar margins towards the outer whorls of the rosette, and the stability of these characteristics from generation to generation.

4 Drawing Sheets

Latin name of the genus and species: The Latin name of the genus and species of the novel variety disclosed herein is *Echeveria agavoides.*

Variety denomination: The inventive variety of *Echeveria agavoides* disclosed herein has been given the variety denomination 'AMIECH2104'.

BACKGROUND OF THE INVENTION

Parentage: 'AMIECH2104' is a seedling selection resulting from the open pollination of a plurality of unnamed *Echeveria agavoides* plants (unpatented). The crossing is believed to have occurred in the spring of 2018 at a commercial greenhouse in Heerhugowaard, the Netherlands. In the summer of 2019, one seedling from said cross was observed to exhibit unique foliage and growth characteristics when compared to the parent plants and all other progenies. The seedling was isolated for further evaluation to confirm the distinctness and stability of the characteristics first observed. After confirming the stability of the unique characteristics first observed, the new plant was selected for commercialization and given the name, 'AMIECH2104'.

Asexual Reproduction: Asexual reproduction of the new cultivar 'AMIECH2104', by way of rooting leaf cuttings, was first initiated in the autumn of 2019 at the inventor's commercial greenhouse in Heerhugowaard, the Netherlands. Through four subsequent generations, the unique features of this cultivar have proven to be stable and true to type.

SUMMARY OF THE INVENTION

The cultivar 'AMIECH2104' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2104'. These characteristics in combination distinguish 'AMIECH2104' as a new and distinct *Echeveria agavoides* cultivar:

1. 'AMIECH2104' exhibits a flattened globular plant profile with foliage loosely arranged in a basal rosette; and
2. 'AMIECH2104' exhibits thick, strong foliage that is conspicuously curled upward distally; and
3. 'AMIECH2104' exhibits light yellow-green to green juvenile foliage with very light greyed-green margins at the center of the rosette; and
4. 'AMIECH2104' exhibits foliage which becomes progressively darker as it matures, transitioning to dark greyed-green with greyed-orange foliar margins, towards the outer whorls of the rosette.

BOTANICAL DESCRIPTION OF THE PLANT

Figure 1:
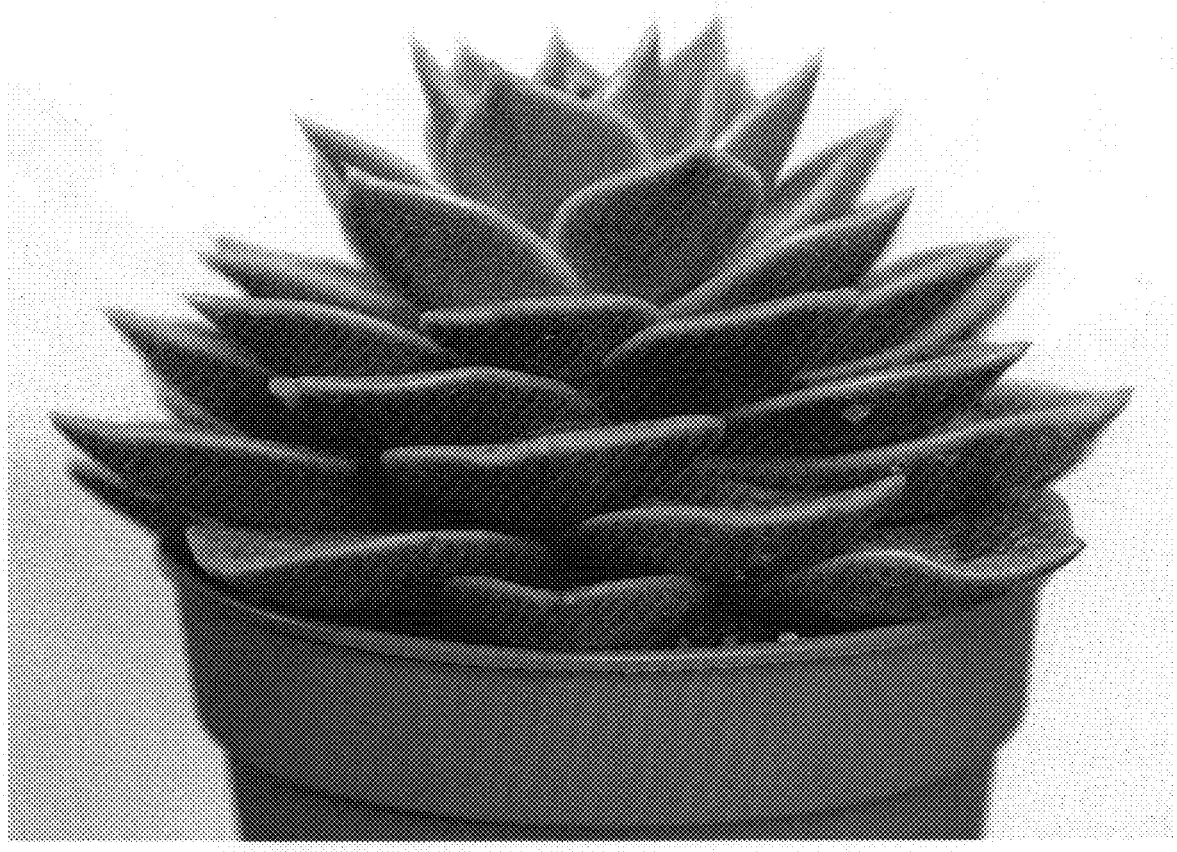
FIG. 1 illustrates, as nearly true as it is reasonably possible to make the same in color photographs of this type, an exemplary plant of 'AMIECH2104' grown in a commercial greenhouse in Heerhugowaard, the Netherlands. This plant is approximately 35 weeks old, shown planted in a 12 cm container.
Figure 2:
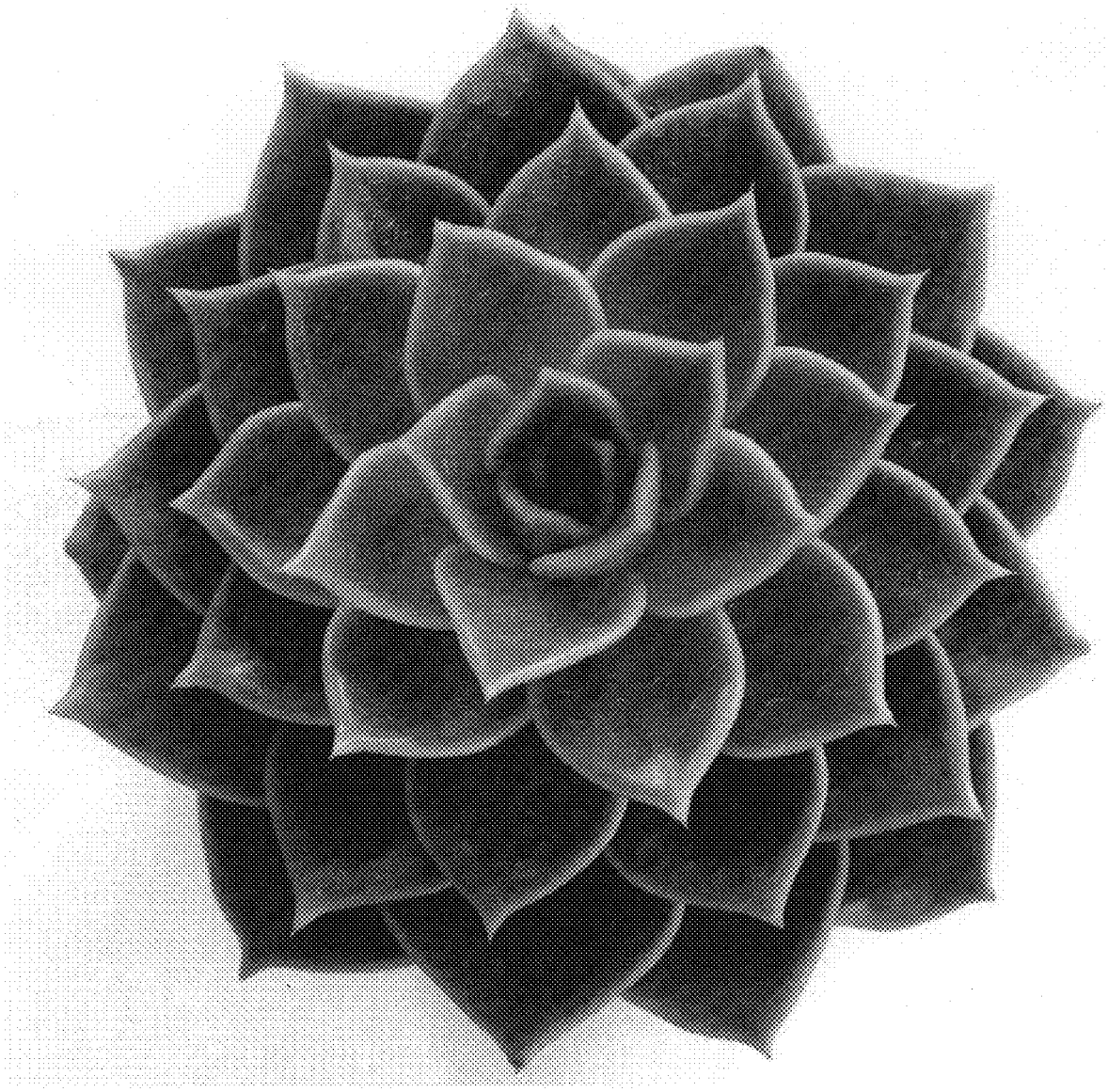
FIG. 2 illustrates, as nearly true as it is reasonably possible to make the same in color photographs of this type, the typical foliage arrangement of 'AMIECH2104.
Figure 3:
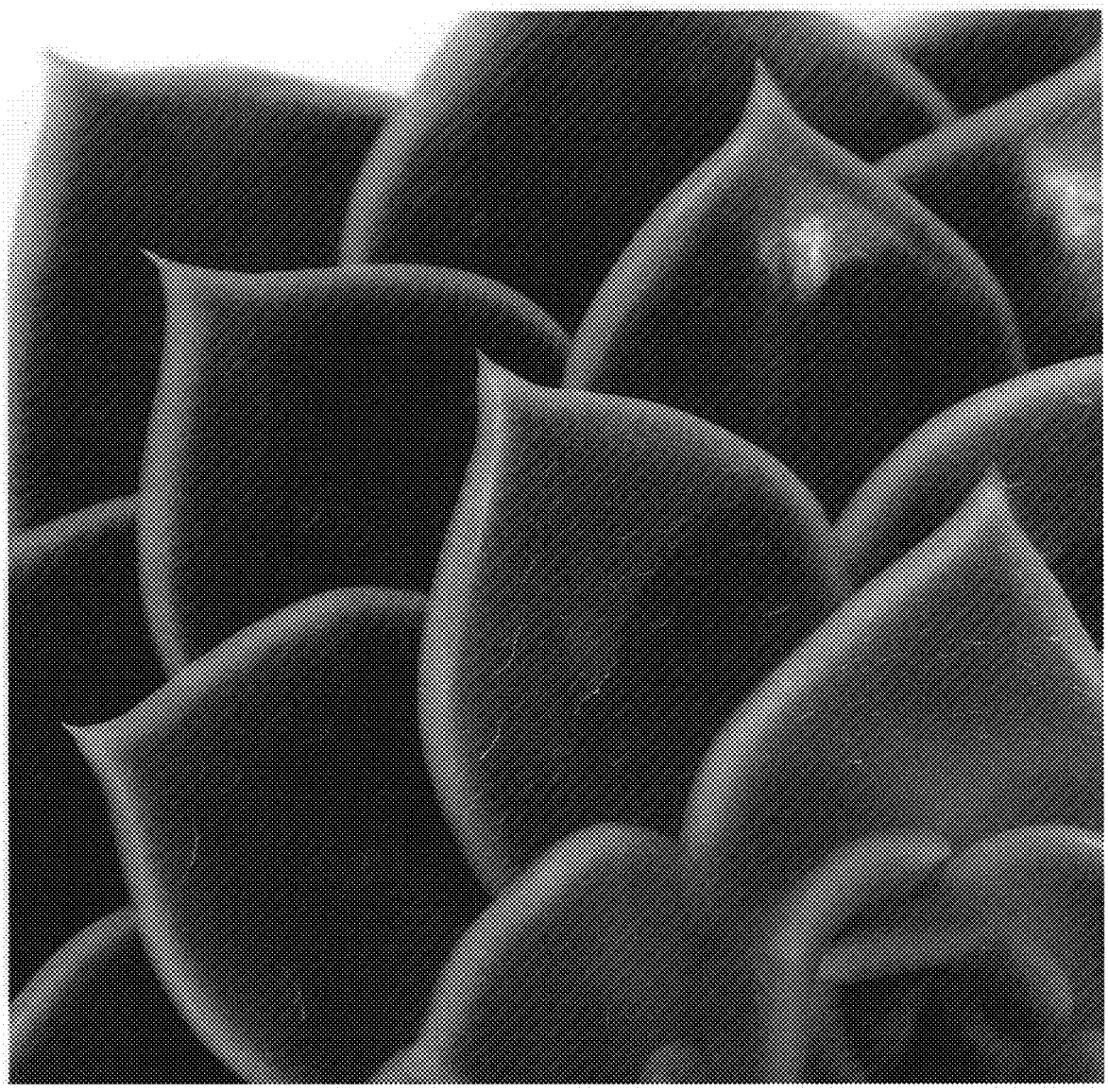
FIG. 3 illustrates, as nearly true as it is reasonably possible to make the same in color photographs of this type, the adaxial surface of the mature foliage 'AMIECH2104'.
Figure 4:
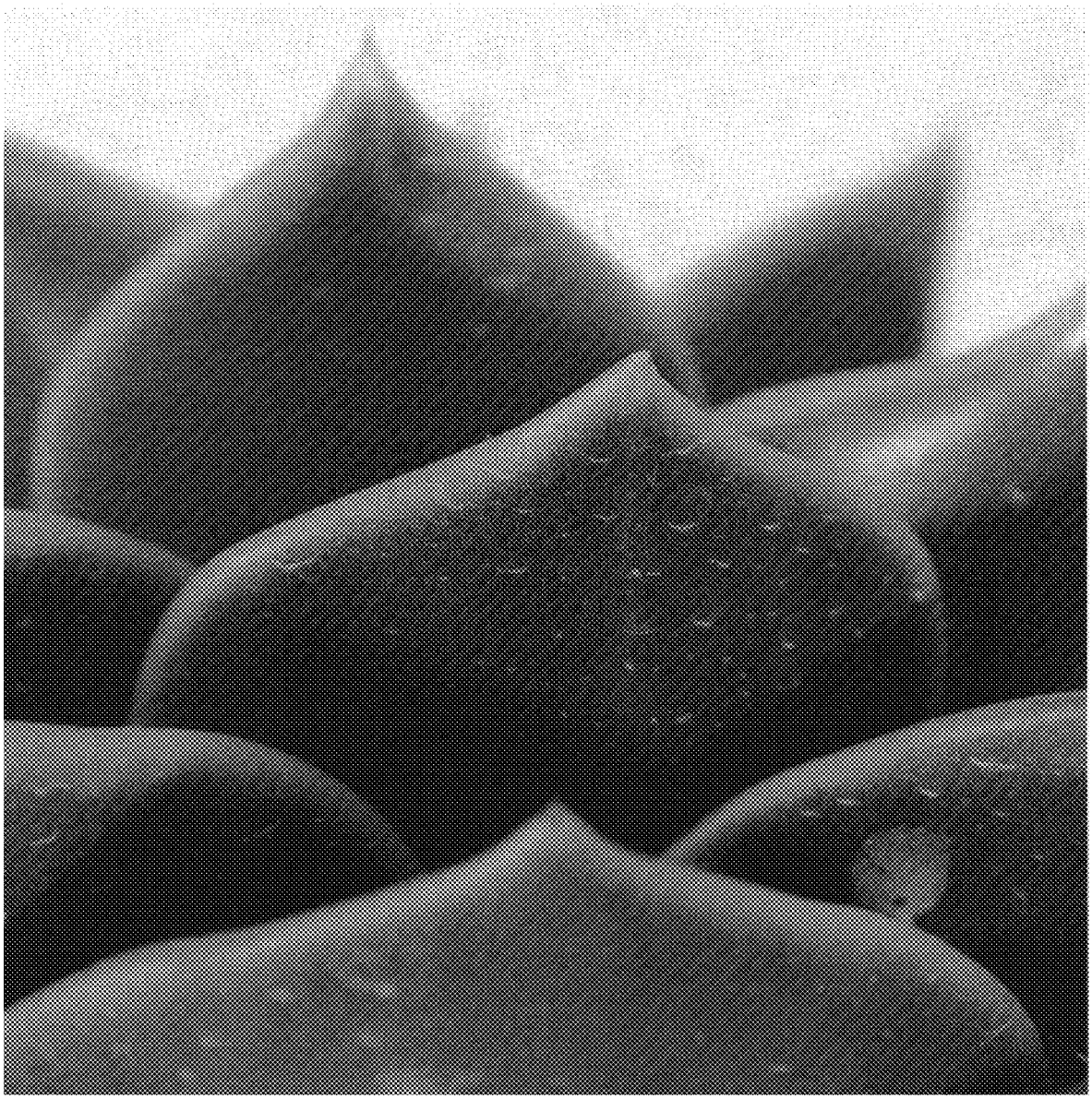
FIG. 4 illustrates, as nearly true as it is reasonably possible to make the same in color photographs of this type, the abaxial surface of the mature foliage 'AMIECH2104'.

The following observations and measurements made in February of 2022 describe averages from a sample set of six specimens of 35-week-old 'AMIECH2104' plants grown in 12 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2104' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH2104' and comparisons with the typical phenotype of the parent plants and closest known comparator are provided below.

Plant description:

*Growth habit*.—Succulent perennial with foliage growing in a non-branched basal rosette.

*Plant shape*.—Flattened globular.

*Height from soil level to top of foliar plane*.—8.7 cm.

*Plant spread*.—Average of 14.5 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in a 7 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosette; no main branches or lateral branches present.

Foliage:

*Arrangement*.—Rosette.

*Division*.—Simple.

*Attachment*.—Sessile.

*Quantity*.—Approximately 50 leaves per rosette.

*Shape*.—Obovate.

*Dimensions*.—5.9 cm long, 3.4 cm wide, and 1.1 cm thick, on average.

*Aspect*.—Very slightly concave and slightly curled upward, distally.

*Attitude*.—Juvenile foliage at the center of the rosette is held upward and outward; foliage becomes progressively more relaxed towards the outer whorls of mature foliage which are approximately 25 degrees from horizontal.

*Apex*.—Broad apiculate.

*Base*.—Cuneate.

*Margin*.—Entire.

*Pubescence, texture and luster of the adaxial surface*.—Smooth, glabrous, and moderately glossy.

*Pubescence, texture and luster of the abaxial surface*.—Smooth, glabrous, and moderately glossy.

*Color*.—Juvenile foliage, adaxial surface — Nearest to a mixture of green and yellow-green, RHS 138A and 147B; fading to greyed-green towards the base, nearest to a combination of RHS 193A and 193B; margins are greyed-green, nearest to a combination of RHS 193C and 193D, and becoming lightly suffused with greyed-red distally, nearest to a mixture of RHS 182B and 182C. Juvenile foliage, abaxial surface — Yellow-green, nearest to a RHS 147B; fading to greyed-green towards the base, nearest to a combination of RHS 193A and 193B; margins are greyed-green, nearest to a combination of RHS 193C and 193D, and becoming lightly suffused with greyed-red distally, nearest to a mixture of RHS 182B and 182C. Mature foliage, adaxial surface — Nearest to a mixture of yellow-green to greyed-green, RHS 147A and 189A yet closest to RHS 189A; fading to a mixture of yellow-green and greyed-green towards the base, nearest to RHS 148D and 194C; margined greyed-orange, nearest to RHS N170D, and becoming lightly suffused with greyed-orange distally, nearest to RHS 185B. Mature foliage, abaxial surface — Greyed-green, nearest to a combination of RHS 197A and 197B; fading to yellow-green towards the base, nearest to RHS 148D; margined greyed-orange, nearest to RHS N170D, and becoming lightly suffused with greyed-purple distally, nearest to RHS 185B. Venation, adaxial surface — No visible venation. Venation, abaxial surface — No visible venation.

*Petiole*.—No petiole; leaves are sessile.

Inflorescence: No flowering has been observed to date.

Comparisons With the Parent Plants and Closest Known Comparator

Plants of the new cultivar 'AMIECH2104' differ from the parents, unnamed *Echeveria agavoides* plants (not patented), in the following characteristics described in Table 1 below. The pollen parent is believed to also be an *Echeveria agavoides*

TABLE 1

| Characteristic | 'AMIECH2104' | The seed parent. |
|---|---|---|
| Foliage length. | Shorter than the seed parent. | Longer than 'AMIECH2104'. |
| General coloration of the rosette. | Light green at the center of the rosette, becoming progressively darker green to greyed-green towards the outer whorls which are a dark greyed-green. | Light yellow-green and lightly covered with a very thin layer of very light greyed-green epicuticular wax. |

TABLE 1-continued

| Characteristic | 'AMIECH2104' | The seed parent. |
|---|---|---|
| General coloration of the foliar margins. | Very light greyed-green. | Green. |

Comparisons With the Closest Known Comparator

Plants of the new cultivar 'AMIECH2104' differ from the closest known commercial comparator, *Echeveria* hybrid 'Mira' (not patented), in the following characteristics described in Table 2 below.

TABLE 2

| Characteristic | 'AMIECH2104' | 'Mira' |
|---|---|---|
| Foliage size. | Larger than 'Mira'. | Smaller than 'AMIECH2104'. |
| Foliage strength. | Stronger than 'Mira'. | Weaker than 'AMIECH2104'. |
| General coloration of the rosette. | Light green at the center of the rosette, becoming progressively darker green to greyed-green towards the outer whorls which are a dark greyed-green. | Light green at the center of the rosette and slightly darker green to greyed-green towards the outer whorls. |

That which is claimed is:

1. A new and distinct variety of *Echeveria agavoides* plant named 'AMIECH2104', substantially as described and illustrated herein.

* * * * *